(12) United States Patent
Reeves et al.

(10) Patent No.: US 7,384,401 B2
(45) Date of Patent: *Jun. 10, 2008

(54) APPARATUS AND METHOD OF USE FOR IDENTIFYING AND MONITORING WOMEN AT RISK OF DEVELOPING OVARIAN SURFACE EPITHELIUM DERIVED CARCINOMAS

(75) Inventors: William H. Reeves, Ft. Lauderdale, FL (US); Jonathan Reeves, Yellow Springs, OH (US); Louis Keith, Chicago, IL (US)

(73) Assignee: Lifeline Biotechnologies, Inc., Reno, NV (US)

( * ) Notice: Subject to any disclaimer, the term of this patent is extended or adjusted under 35 U.S.C. 154(b) by 568 days.

This patent is subject to a terminal disclaimer.

(21) Appl. No.: 10/889,262

(22) Filed: Jul. 12, 2004

(65) Prior Publication Data

US 2004/0249305 A1  Dec. 9, 2004

Related U.S. Application Data

(62) Division of application No. 10/035,845, filed on Dec. 24, 2001, now Pat. No. 7,056,293.

(51) Int. Cl.
*A61B 10/00* (2006.01)
*A61B 1/00* (2006.01)

(52) U.S. Cl. .................. 600/569; 600/114; 600/153; 600/562

(58) Field of Classification Search ............... 600/160, 600/178, 182, 310, 342, 478, 562, 569, 570, 600/104, 153, 114
See application file for complete search history.

(56) References Cited

U.S. PATENT DOCUMENTS

| | | | |
|---|---|---|---|
| 4,700,694 A | 10/1987 | Shishido | |
| 5,073,857 A | 12/1991 | Peters et al. | |
| 5,083,549 A | 1/1992 | Cho et al. | |
| 5,156,590 A | 10/1992 | Vimar | |
| 5,458,606 A | 10/1995 | Cohen et al. | |
| 5,871,941 A | 2/1999 | Auerperg | |
| 5,873,814 A | 2/1999 | Adair | |
| 6,113,576 A | 9/2000 | Dance et al. | |
| 6,156,006 A | 12/2000 | Brosens et al. | |
| 6,405,074 B1 | 6/2002 | Banerjee | |
| 7,056,293 B2 * | 6/2006 | Reeves et al. | 600/569 |
| 2002/0087047 A1 * | 7/2002 | Remijan et al. | 600/109 |
| 2002/0165467 A1 | 11/2002 | Rutenberg | |
| 2003/0083552 A1 | 5/2003 | Remijan | |

* cited by examiner

*Primary Examiner*—Max Hindenburg
*Assistant Examiner*—Jonathan M Foreman
(74) *Attorney, Agent, or Firm*—R. William Graham

(57) ABSTRACT

An apparatus and method of use thereof for identifying and monitoring women at risk of developing OSE-derived carcinomas is provided. The apparatus includes an introducer needle configured to be capable of insertion into a female such that a terminal end of the needle is positioned adjacent an ovary of the female, a microendoscope having an optic fiber which is operably insertable into the needle in a manner to enable an image of the ovary to be obtained therethrough, and a tissue removing member operably co-insertable into the needle with the optic fiber therein to enable removal of ovarian tissue cells with minimal deleterious effect to the ovary.

9 Claims, 3 Drawing Sheets

APPARATUS AND METHOD OF USE FOR IDENTIFYING AND MONITORING WOMEN AT RISK OF DEVELOPING OVARIAN SURFACE EPITHELIUM DERIVED CARCINOMAS

This is a divisional application of U.S. Ser. No. 10/035,845 filed Dec. 24, 2001 now U.S. Pat. No. 7,056,293.

BACKGROUND OF THE INVENTION

1. Field of the Invention

This application relates to a screening methodology for identifying individuals having a predisposition to develop or have ovarian cancer.

2. Prior Art

Ovarian cancer remains notoriously difficult to detect in its early stages. Over 80% of female ovarian carcinomas are thought to arise from the OSE. OSE-derived carcinomas are the fifth or sixth most frequent malignancy in American women and the five year survival rate of patients with ovarian cancer is less than 40%. A significant need therefore remains for a new screening test for identifying and monitoring women at risk of developing OSE-derived carcinomas.

There exist various tests for the presence of female specific cancers including, for example, mammography for breast cancer and pap smears for cervical cancer. Prior hereto, inadequate methodology exists for ovarian cancer screening.

One commonly used test for ovarian cancer involves measuring the phenotypic expression of the CA125 antigen in overtly normal ovarian surface epithelium cells propagated in vitro. Recently, the use of tumor markers, such as serous cystadeno carcinoma ovarian tumor associated antigen CA125 for monitoring the progression of ovarian surface epithelium (OSE) carcinomas, has improved diagnostic and prognostic accuracy in the management of ovarian carcinomas. Elevated serum levels of CA125 antigen are detectable in approximately 80-90% of ovarian cancer patients. The presence of CA125 is typically detected by radioimmunoassays employing monoclonal antibodies such as OC125 which bind specifically to the CA125 antigenic determinant.

Although the measurement of serum CA125 levels is an effective tool for monitoring the progression of ovarian cancers, it does not aid in providing a screening test as a predictive marker for identifying healthy women at increased risk for ovarian cancer, or for detection of very early stages of the disease.

Genetic analysis is another helpful methodology to determine women who are at an increased risk of developing ovarian cancer. This alone, however, is insufficient and additional contributing factors are poorly defined. Of equal importance, a significant number of ovarian cancers arise in women without family histories.

One potential alternative strategy is to identify preneoplastic phenotypic changes in the OSE which could signal a predisposition to development of ovarian tumors. To date, however, little progress has been made in the early detection of such preneoplastic tissue changes and no reliable tumor-associated tissue markers have yet been identified. This lack of information about early changes in the OSE poses a particular problem for women with hereditary ovarian cancer syndromes, in which there is an urgent need to define more reliable criteria for prevention and surveillance. One test uses a scrape method with a laparoscope to gain cell cultures. The cultured cells use the OSE cells in vitro to obtain a population of propagated OSE cells derived from the sample. The expression of CA125 antigen by said propagated OSE cells was measured to indicate the predisposition of ovarian cancer. This screening method misses nearly one-half of early stage cancers.

Still another test employed uses transvaginal sonograms (ultrasound). This has been effective for determining presence of existing abnormalities with the tissue, but transvaginal ultrasound cannot distinguish between early stage cancers and other abnormalities such as benign cysts.

In contrast, pap smear tests for automated screening of cytological smears for dense, possibly malignant cells have proven to be useful in detecting other cancers, such as cervical. However, the pap smear test is presently not used in the area of ovarian cancer detection for the lack of a suitable tissue extraction method. A pap smear test typically includes a specimen slide for receiving a cytological smear and a microscope for viewing the image of the smear.

The present invention provides a solution to the deficiencies in the art.

SUMMARY OF THE INVENTION

It is an object of the present invention to improve screening tests for identifying and monitoring women at risk of developing OSE-derived carcinomas.

It is another object to provide a device to aid in the screening test for identifying and monitoring women at risk of developing OSE-derived carcinomas.

According to the present invention, there is disclosed an apparatus and method of use thereof for identifying and monitoring women at risk of developing OSE-derived carcinomas. The apparatus includes an introducer needle configured to be capable of insertion into a female such that a terminal end of the needle is positioned adjacent an ovary of the female, a microendoscope having an optic fiber which is operably insertable into the needle in a manner to enable an image of the ovary to be obtained therethrough, and a tissue removing member operably co-insertable into the needle with the optic fiber therein to enable removal of ovarian tissue cells with minimal deleterious effect to the ovary. The needle preferably is equipped with a stylet.

The microendoscope includes a housing having an optic fiber operably extending from the housing and substantially the length of the needle to enable insertion into the needle such that ends of the needle and optic fiber are generally co-terminus. Operably connected to the housing is a camera for viewing an image seen through the optic fiber. The camera is preferably connected to a touch screen monitor with software to enable viewing of the image and recordation of physician notes into a data file associated with the viewed image. A fiber optic light source is operably connected to the housing such that the optic fiber is illuminated. The housing further includes a port through which the tissue removing member can be inserted. The tissue removing member can be an ovarian cytology brush.

The method of the invention includes the steps inserting an introducer needle having a stylet therein into a female such that a terminal end of the needle is positioned adjacent an ovary of the female, removing the stylet, operably inserting an optic fiber of a microendoscope into the needle in a manner to enable an image of the ovary to be obtained therethrough, and viewing an image through the use of the microendoscope. The method further includes operably inserting a tissue removing member into the needle and removing ovarian tissue cells with minimal deleterious effect to the ovary. The method is further characterized such that the optic fiber and the tissue removing member are co-inserted within the needle. The method further includes employing a viewing monitor with an operably associated computer to aid in viewing the image and ovarian tissue removal. Further, the method calls for employing software residing on the computer to record the image and physician notes in a data file on the computer.

Other objects and advantages will be readily apparent to those skilled in the art upon viewing the drawings and reading the detailed description hereafter. The preferred embodiment of the present invention will now be described with reference to the drawings.

DETAILED DESCRIPTION OF THE INVENTION

Figure 1:
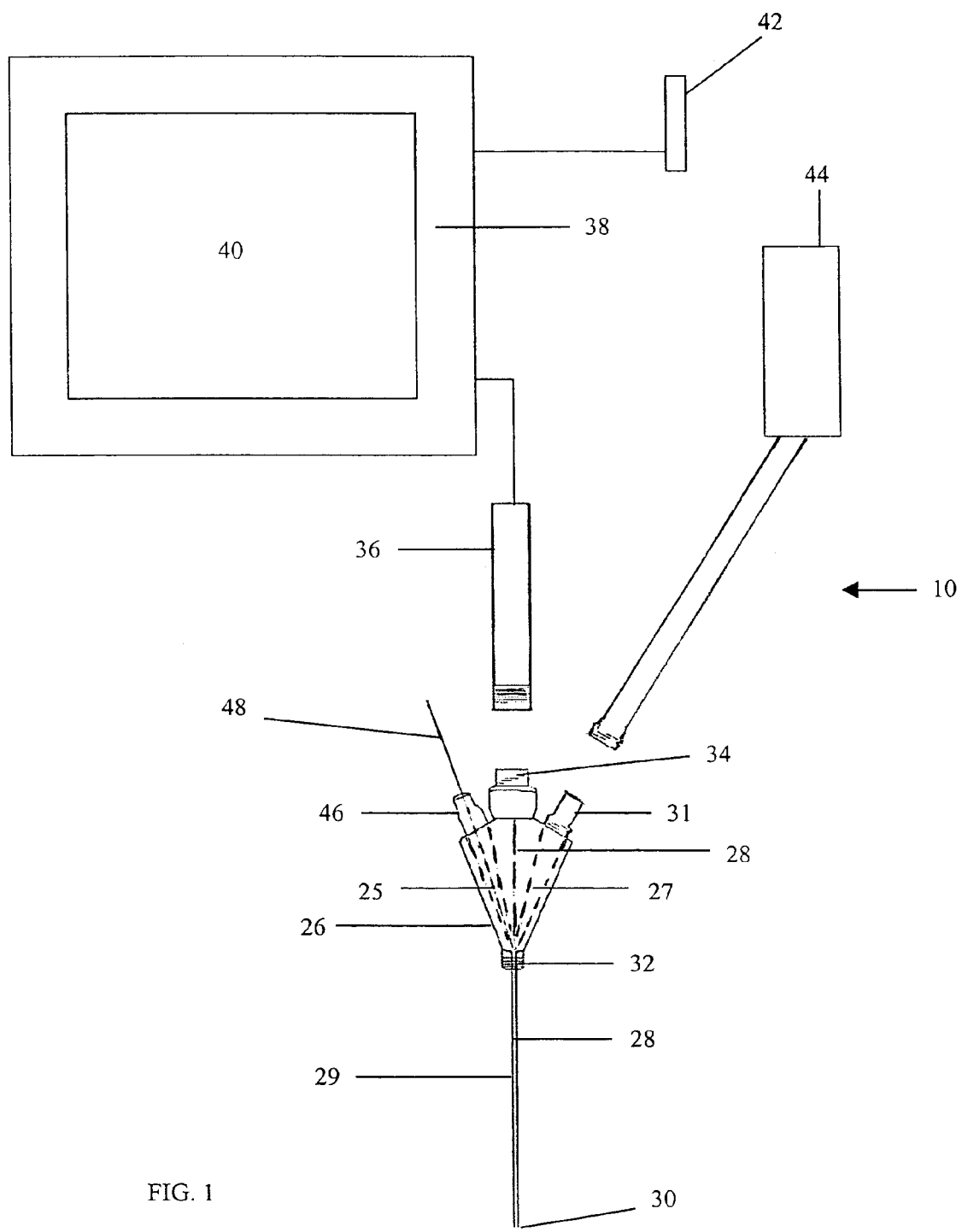
FIG. 1 is a schematic view of the present invention.
Figure 2:
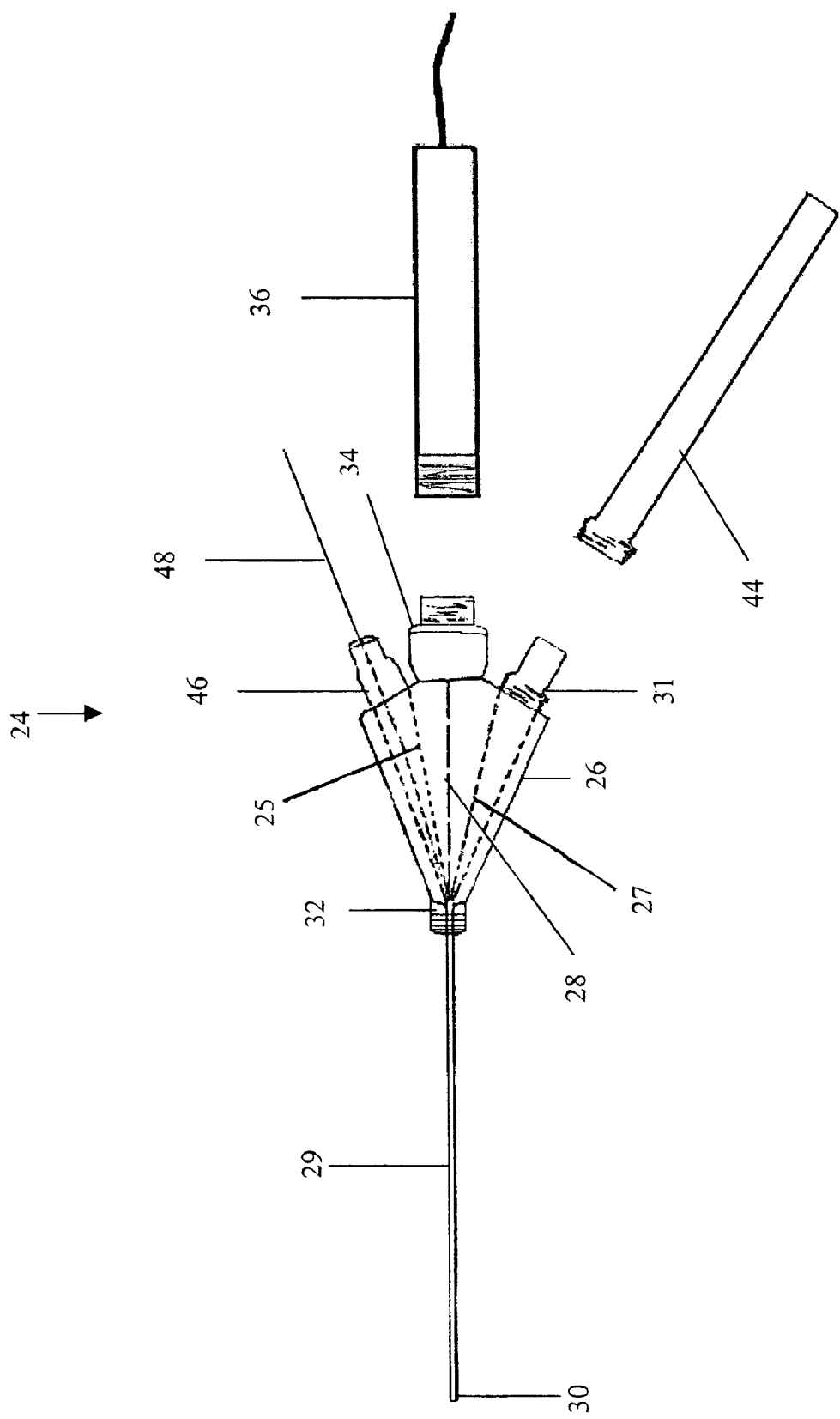
FIG. 2 is a schematic view of a part of a microendoscope of the present invention.
Figure 3:
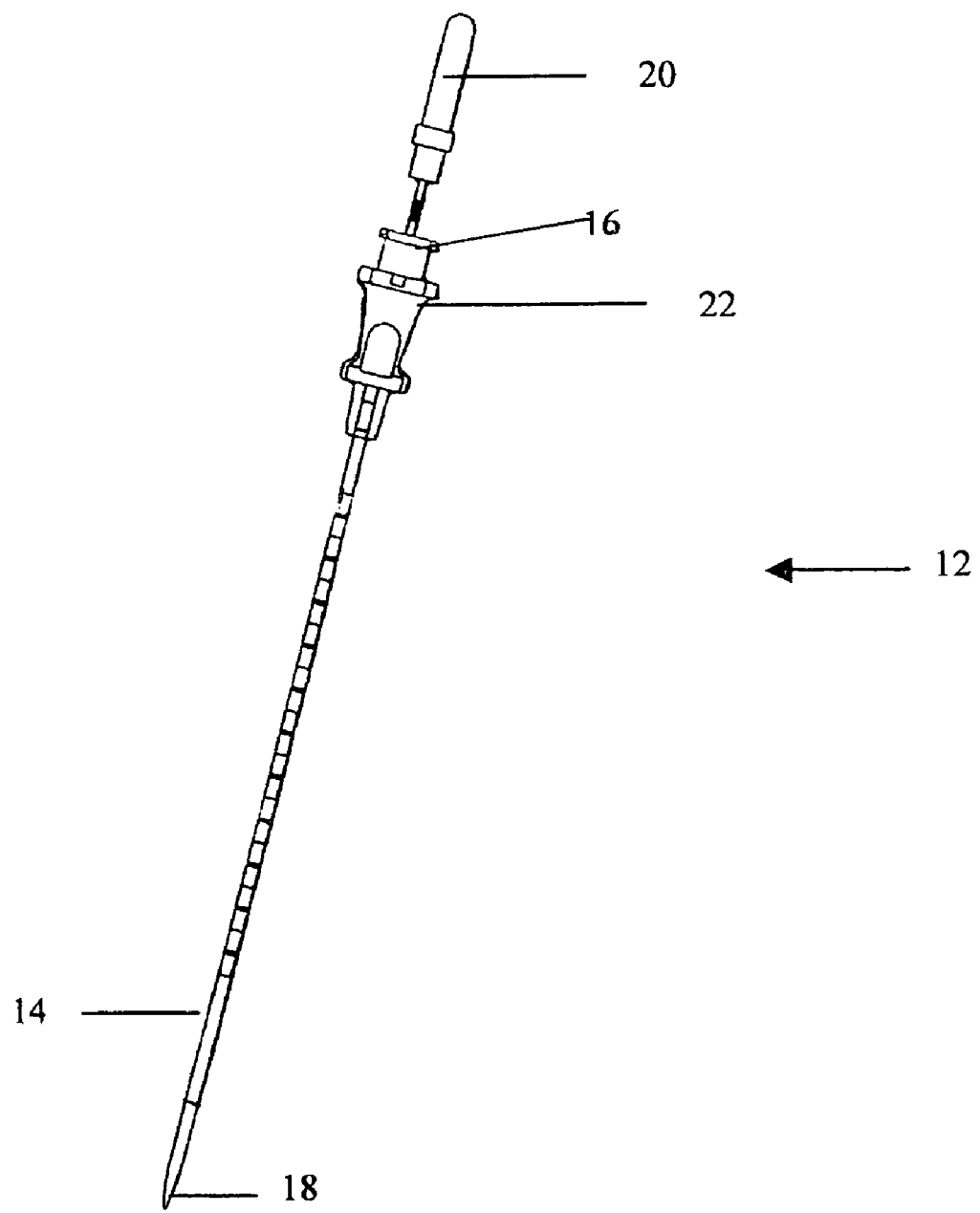
FIG. 3 is a schematic view of an introducer needle for use with the present invention.

Referring now to the drawings, the present invention is directed to an apparatus and method of use thereof for identifying and monitoring women at risk of developing OSE-derived carcinomas and is generally designated by the numeral 10. The apparatus 10 includes an introducer needle 12 configured to be capable of insertion into a female such that a terminal end 14 of the needle is positioned adjacent an ovary of the female. The needle preferably is equipped with a stylet 16 which has a tip 18 which extends through the needle 12 and a handle 20. The stylet 16 prevents unwanted material from entering the needle 12 until the end 14 of the needle 12 is in its usable position. Further, the needle has a neck 22 which is formed in a manner to permit sealable connection thereto.

The invention includes a microendoscope 24 which includes a housing 26 preferably has three channels formed therein which are separated by inner partitions 25 and 27 and communicate with an open surface end 32. Each channel defines a separate, continuous and unobstructed path to the open surface 32. An optic fiber 28 operably extends through one channel of housing 26 and out the end 32 and through a flexible tubing 29 which is connected to the housing 26. The optic fiber 28 is substantially the length of the needle 12 to enable insertion therein such that the end 14 of the needle 12 and end 30 of the optic fiber 28 are generally co-terminus. Preferably, the optic fiber 28 can include a bundle of fibers. In this way, when the optic fiber 28 is operably inserted into the needle 12 it can enable an image of the ovary to be obtained therethrough.

The open surface end 32 is preferably of a connectable type, i.e., a luer lock, which enables a scalable connection with the neck 22 of the needle 12 when the stylet 16 is removed and tubing 29 and optic fiber 28 are inserted therein. The luer lock 32 connection can preferably be chrome plated glass.

The tubing 29 can preferably be made of Nitinol and is used as the outer sheathing of the optic fiber 28 because it is less likely to kink than stainless steel tubing. This will prolong the life of the microendoscope 24.

Operably connected to a camera mount 34 of the housing 26 is camera 36 for viewing an image seen through the optic fiber 28. The camera 36 is preferably connected to an integrally formed computer 38 with a touch screen monitor 40. The computer 38 has software to enable viewing of the image and recordation of physician notes into a data file associated with the viewed image. The computer 38 has a microphone 42 operably associated therewith and the software includes a voice recognition capacity to enable a physician to have their verbal notes automatically transcribed and associated in the data file with the viewed image.

The housing 26 can be black anodized aluminum. The camera connector 34 can preferably be natural ultem. There is provided a light post 31 which can be preferably stainless steel available from ACMI. All of these components are preferably USP Class VI tested and/or recognized biocompatible material. The various connections to housing 26 provide a relatively unique v-type body design to make it easy to hold on to the microendoscope 24 and as a second design characteristic, it allows for the three functions to be incorporated into the handle. These functions are multiple instrument channel insertion, imaging and lighting. A fiber optic light source 44 is operably connected to the housing 26 such that the optic fiber 28 is illuminated.

Another port 46 is provided on the housing 26 to receive a tissue removing member 48 in a manner wherein the member 48 is operably co-insertable into the needle 12 with the optic fiber 28 (with tubing 29 covering) therein. The tissue removing member 48 can be an ovarian cytology brush which enables removal of ovarian tissue cells with minimal deleterious effect to the ovary. The cytology brush can be made of a stainless steel wire with nylon or stainless steel bristles, preferably it will be made of stainless steel wire. The length of the complete cytology brush device can be for example about 24 inches. The portion of the brush 48 that extends beyond the end 14 will be about one inch long.

The preferred method of the invention is as follows. The patient is in the stirrups for a general gynecologic examination. A speculum of appropriate size is used to visualize the cervix. A cervical pap smear is obtained in the usual manner.

After this is completed, the cervix and the vaginal fornices are swabbed with Betadin for the purpose of disinfection. A single or double tooth tenaculum is then placed on the anterior or posterior cervical lip depending upon which site is more easily assessable and better affords a grasp. Local anesthesia may or may not be used depending on operator and patient preference.

The cervix is then put on a stretch and manipulated to the patient's right side thereby exposing the left vaginal fornix. The 18 gauge UTW 20 cm (needle 12) introducer is then inserted into the left fornix for approximately 1-2 cm. At this point, the stylet 16 is removed and the microendoscope 24 advanced. Because the microendoscope 24 is already connected to the camera 36, the light source 44 can be turned on and further passage of the microendoscope 24 into the abdominal cavity is under direct vision. As the microendoscope 24 advances, it is manipulated so that the ovary on the left side is visualized. Once the ovary is visualized, the ovarian surface brush 48 is advanced through the operative channel, placed against the ovary, rotated and removed. The sample is then transferred to appropriate media carriage tubes. Should the operator wish to repeat the brushings, a second (or even third) brush can be used in order to facilitate obtaining samples from different ovarian surface sites in a sterile manner.

The introducer needle 12 and microendoscope 26 are then removed. The microendoscope 26 is removed from the introducer needle 12 and maintained in a sterile condition. The introducer needle 12, previously maintained in a sterile condition, is reinserted into the needle and then procedure is repeated on the patient's right side. After the procedure, the introducer needle 12 can be discarded and a new introducer needle 12 obtained for the next patient. Thus, the introducer needle 12 can preferably be of a disposable material nature, whereas the microendoscope 24 is of a reusable and sterilizable material composition.

Throughout the operation, the microendoscope 24 is operably connected to the computer 38. Thus, the operator views the interior of the abdominal cavity using the flat screen 40 just as done in laparoscopy in hysteroscopy. Cervical pap smears done in a similar nature have reduced cervical cancer deaths by 70% in the last two decades.

The above described embodiments are set forth by way of example and are not for the purpose of limiting the present invention. It will be readily apparent to those skilled in the art that obvious modifications, derivations and variations can be made to the embodiments without departing from the scope of the invention. Accordingly, the claims appended hereto should be read in their full scope including any such modifications, derivations and variations.

What is claimed is:

1. A method for detecting identifying and monitoring women at risk of developing OSE-derived carcinomas, which includes the following steps:

Obtaining a pap smear from a female patient;

Exposing a vaginal fornix of the patient;

Employing a device having an introducer needle configured to operably co-receive an optic fiber and a tissue removing member therethrough and configured for insertion into the female patient such that a terminal end of said needle is positioned adjacent an ovary of the female patient;

Employing a microendoscope having an optic fiber operably extending therefrom and operably inserting said optic fiber into said needle in a manner to enable an image of the ovary to be obtained therethrough;

Inserting a tissue removing member through said microendoscope in a manner to be operably co-insertable into said introducer needle with said optic fiber therein to enable removal of ovarian tissue cells with minimal deleterious effect to the ovary;

Inserting said introducer needle into the fornix to advance said microendoscope to enable visualization of the ovary;

Advancing said tissue removing member to contact the ovary in a manner to enable OSE tissue cells to be obtained therewith; and Removing the tissue removing member and OSE tissue cells from said device for analysis.

2. The method of claim 1, wherein said needle is equipped with a stylet which extends through said needle to block unwanted material from entering said needle and includes an end which seats against a neck of said needle and which can be gripped to permit removal of said style.

3. The method of claim 2, whereupon removal of said stylet, said optic fiber is further characterized to extend out of said microendoscope, wherein said microendoscope is sealably connectable to said neck of said needle with said optic fiber extending into said needle.

4. The method of claim 3, wherein said microendoscope includes a fiber optic light source operably connected thereto such that said optic fiber is illuminated and a camera operably connected for viewing an image seen through said optic fiber.

5. The method of claim 4, wherein said camera is connected to a monitor operably connected to a computer having software to enable viewing of said image and recordation of physician notes into a data file associated with said viewed image.

6. The method of claim 5, wherein said monitor and said computer are integrally formed in a touch screen monitor computer.

7. The method of claim 6, wherein said computer includes a microphone operably connected thereto and said software includes voice recognition and is operably associated with said microphone to permit said notes to be recorded via said voice recognition software.

8. The method of claim 1, wherein said tissue removing member is an ovarian cytology brush.

9. The method of claim 1, wherein the step of inserting the needle is characterized as inserting the needle into the fornix between about 1 to 2 centimeters.

* * * * *